US009808170B2

(12) United States Patent
Lane et al.

(10) Patent No.: US 9,808,170 B2
(45) Date of Patent: Nov. 7, 2017

(54) ELECTRODE WITH CHARGE-OPERATED INDICATOR

(71) Applicant: Welch Allyn, Inc., Skaneateles Falls, NY (US)

(72) Inventors: John A. Lane, Weedsport, NY (US); Benjamin Freer, Rochester, NY (US); David E. Quinn, Auburn, NY (US); Frederik W. Kroon, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 877 days.

(21) Appl. No.: 13/836,738

(22) Filed: Mar. 15, 2013

(65) Prior Publication Data

US 2014/0275823 A1    Sep. 18, 2014

(51) Int. Cl.
*A61B 5/04*   (2006.01)
*A61B 18/16*  (2006.01)
(Continued)

(52) U.S. Cl.
CPC ............ *A61B 5/04087* (2013.01); *A61B 5/01* (2013.01); *A61B 5/7221* (2013.01); *A61B 5/74* (2013.01);
(Continued)

(58) Field of Classification Search
CPC . A61B 5/0402; A61B 5/0006; A61B 5/04087; A61B 5/01; A61B 5/7203;
(Continued)

(56) References Cited

U.S. PATENT DOCUMENTS

| 4,325,384 A * | 4/1982 | Blaser | A61B 5/04004 |
| | | | 128/902 |
| 4,522,211 A * | 6/1985 | Bare | A61B 5/04087 |
| | | | 439/325 |

(Continued)

FOREIGN PATENT DOCUMENTS

| GB | 1147354 A | 4/1969 |
| GB | 2418365 A | 3/2006 |

(Continued)

OTHER PUBLICATIONS

Invivo Corporation, "Invivo Expression, MRI Patient Monitoring Systems", 2009, Part No. 865214.

(Continued)

*Primary Examiner* — Joseph Stoklosa
*Assistant Examiner* — Brian M Antiskay
(74) *Attorney, Agent, or Firm* — Lee & Hayes, PLLC

(57) ABSTRACT

An electrode includes separate first and second electrical contacts to contact the skin of a subject. A charge-holding structure is electrically connected between the first and second contacts. An indicator is operatively coupled to the charge-holding structure so that the indicator changes visibly in response to a change in the charge stored in the charge-holding structure. The electrode can include a rectifier across the contacts. A container for electrodes includes an electrical supply and a plurality of receptacles for electrodes so that a voltage difference is maintained across conductors of each receptacle (and contacts of an electrode therein) for at least one week. A method of making electrodes includes arranging the contacts over a support, connecting the charge-holding structure between them, arranging the indicator over the support, and charging the charge-holding structure so that the indicator has a first visual appearance.

28 Claims, 10 Drawing Sheets

(51) Int. Cl.
*A61B 5/0408* (2006.01)
*A61B 5/01* (2006.01)
*A61B 5/00* (2006.01)

(52) U.S. Cl.
CPC ............... *A61B 2560/0462* (2013.01); *A61B 2562/0257* (2013.01)

(58) Field of Classification Search
CPC ... A61B 5/0416; A61B 5/6843; A61B 5/7721; A61B 2562/0214
USPC ......... 600/372, 382, 384, 386–393, 508–509
See application file for complete search history.

(56) References Cited

U.S. PATENT DOCUMENTS

| | | | |
|---|---|---|---|
| 5,002,064 A | 3/1991 | Allain et al. | |
| 5,025,808 A | 6/1991 | Hafner | |
| 5,402,884 A * | 4/1995 | Gilman | A61N 1/046 206/438 |
| 5,645,577 A | 7/1997 | Froberg et al. | |
| 5,862,803 A * | 1/1999 | Besson | A61B 5/14552 128/903 |
| 7,198,341 B1 | 4/2007 | Rast | |
| 7,340,294 B2 | 3/2008 | Gray | |
| 7,791,489 B2 | 9/2010 | Gelbman et al. | |
| 7,857,507 B2 | 12/2010 | Quinn et al. | |
| 7,907,995 B2 | 3/2011 | Nagata et al. | |
| 8,079,756 B2 | 12/2011 | Quinn et al. | |
| 8,086,300 B2 | 12/2011 | Herlerkson | |
| 8,099,166 B2 | 1/2012 | Schuller et al. | |
| 8,160,682 B2 * | 4/2012 | Kumar | A61B 5/0006 600/509 |
| 8,352,012 B2 * | 1/2013 | Besio | A61B 5/04004 600/383 |
| 2005/0277841 A1 * | 12/2005 | Shennib | A61B 5/0444 600/511 |
| 2007/0002007 A1 | 1/2007 | Tam | |
| 2007/0235295 A1 | 10/2007 | Verma | |
| 2008/0177341 A1 | 7/2008 | Bowers | |
| 2009/0234352 A1 * | 9/2009 | Behnke | A61B 18/16 606/35 |
| 2009/0259137 A1 | 10/2009 | Delic et al. | |
| 2010/0022903 A1 | 1/2010 | Sitzman et al. | |
| 2011/0130636 A1 | 6/2011 | Daniel | |
| 2011/0213261 A1 | 9/2011 | Naware et al. | |
| 2012/0157807 A1 | 6/2012 | Virtanen et al. | |
| 2012/0330126 A1 * | 12/2012 | Hoppe | A61B 5/0002 600/391 |
| 2014/0275924 A1 * | 9/2014 | Min | A61B 18/12 600/377 |

FOREIGN PATENT DOCUMENTS

| | | |
|---|---|---|
| JP | 2009233325 A | 10/2009 |
| WO | 0176466 A2 | 10/2001 |
| WO | 2006061762 A2 | 6/2006 |

OTHER PUBLICATIONS

International Preliminary Report on Patentability for International Application No. PCT/US2013/074545 dated Sep. 24, 2015 (10 pgs.).
International Search Report and Written Opinion for International Application No. PCT/US2014/028195 dated Aug. 12, 2014 (13 pgs.).
International Search Report for International Application No. PCT/US2014/028195 dated Aug. 12, 2014 (3 pgs.).
Electronic Ink Analysis, http://www.inference.phy.cam.ac.uk/pjc51/thesis/pjcthesis_6.pdf; Accessed Date: Jan. 24, 2012 (30 pages).

* cited by examiner

ELECTRODE WITH CHARGE-OPERATED INDICATOR

TECHNICAL FIELD

The present application generally relates to the field of diagnostic patient examination and more specifically relates to skin-contacting electrodes used in medical examination devices to measure properties of subjects or their environments, e.g., electrical activity.

BACKGROUND

An electrocardiogram (ECG) monitoring apparatus is a medical device that receives and processes ECG signals generated by a circulatory system of a person, e.g., the electrical impulses that trigger various phases of a heartbeat. The apparatus typically includes a plurality of patient-contact electrodes ("electrodes," "skin-contact biopotential electrodes," or "SCBEs"), each electrically connected via a wire to a voltage detector. The patient-contact electrodes make physical contact with the person being monitored, e.g., on the person's skin. The ECG electrodes and wires receive and relay ECG signals generated by the person to components of the ECG monitoring apparatus that process the ECG signals.

FIG. 1 is a partially-schematic view of a conventional ECG monitoring apparatus including six ECG patient contact wires 103 connected to respective patient-contact electrodes 101. (Any number of electrodes and wires can be used.) Electrodes 101 are configured to be attached to the skin of a person or other animal (e.g., a dog, cat, bird, or other pet), also referred to as a patient or subject (subject 38, shown in phantom for purposes of orientation throughout this disclosure). Electrodes 101 are shown attached to the left arm, right arm, left leg, and chest of subject 38. ECG unit 186 receives ECG signals generated by the patient (not shown) via ECG wires 103 and processes those signals. ECG unit 186 provides to a caregiver representation(s) of one or more electrode voltage(s) or voltage difference(s). The representation(s) can be, e.g., printouts on graph paper or continually-updated traces on a display screen of ECG unit 186. In carrying out an ECG examination, ECG electrodes 101 can be attached to points on the upper body (e.g., chest and arms) or lower body (e.g., legs) of the patient. Further details regarding the placement and orientation of the electrodes and workings of an ECG apparatus is known to those in the field, such as provided in U.S. Pat. No. 7,618,377B2, incorporated herein by reference.

Skin-contact electrodes based on measuring biopotentials (e.g., electrodes 101) are used in various medical examination apparatus, notably electrocardiograms (ECG or EKG) that measure heart activity. They are also used for electroencephalograms (EEG) that measure brain activity and electromyograms (EMG) that measure the electric potentials generated by skeletal muscles. In the course of examination, some ECG applications use 10 (ten) or more individual wires, each with a corresponding electrode. Moreover, the electrodes used are generally identical to reduce measurement variation and electrode measurement cost. As a result, wires can readily be attached to the wrong electrodes.

Furthermore, many electrodes are provided with an adhesive element that permits an operator to adhere the electrodes to the skin of subject 38. An operator can be, e.g., a medical professional or other caregiver, a subject himself or herself, or a member of the subject's family, e.g., the subject's spouse. Electrode adhesives can have a limited shelf life, after which they will no longer adequately adhere to the subject. An issue is that loose electrodes are not readily identified by the caregiver, creating significant delays and errors in the examination process, whether in the course of a scheduled medical examination in a medical facility or in situations in which an apparatus such as a Holter assembly is worn for longer periods of time.

GB 2418365 A describes skin contact electrodes used with test circuits. Two contact areas are electrically connected through skin contact gel and a conductive backing layer. Before the electrode is applied to a patient, and before the backing layer is removed in preparation for doing so, the impedance through the gel and backing layer between the two contact areas is determined. The condition of the gel is inferred from the determined impedance.

However, this scheme does not permit determining the quality of the connection between the electrode and the patient's skin. The gel condition is determined before the electrode is applied. Even if the gel is in operable condition, it can still fail to make effective electrical contact with the patient due to hair, sweat, skin oil, skin flakes, dirt, or other contaminants on the skin, misapplication of the electrode, or a defect in the electrode. There is, therefore, a continuing need for determining whether an electrode is effectively electrically coupled to a patient, whether initially or over the course of examination.

WO 2008/056309 attempts to address this need by injecting a signal into a patient through a reference electrode. The signal passes through the patient, and the ease of detection of the signal at an electrode other than the reference is an indication of the quality of the connection of that other electrode. However, this scheme requires a reference electrode, and it requires correlating readouts on a display screen attached to ECG unit 186 with the wires and electrodes on the patient's body, which can be an error-prone process. Wires are generally color-coded, but this does not help wholly- or partly-colorblind operators. U.S. Pat. No. 5,042,498 provides LEDs on electrode wires to indicate which wires are attached to poorly-connected electrodes, but these schemes require specialized wires and electrode adapters, and are not useful for circumstances such as home monitoring in which an ECG might be used by a patient instead of a doctor. U.S. Publication No. 20100081950 describes LEDs on the electrodes illuminated in a sequence, e.g., the path of a hand-drawn letter "e" across then around the chest, to visually highlight electrodes connected to the wrong wires. However, this scheme also requires specialized electrode wires and adapters. Moreover, this scheme requires special electrodes, so conventional electrodes cannot be used with a described ECG unit.

There is, therefore, a continuing need of more readily determining whether an electrode has reached the end of its useful life. There is also a need of a way of determining the quality of electrical contact between an electrode and the skin of the patient. There is a further need of doing so in a way that relieves an operator of the need to trace through a myriad of wires in order to identify the appropriate wire and electrode.

BRIEF DESCRIPTION OF THE INVENTION

Furthermore, devices for conducting medical examinations vary greatly in their capabilities. Electricity-measurement devices used by medical professionals in a controlled setting, such as a hospital, can have capabilities significantly greater than small, portable devices (such as Holters) that conduct tests routinely and sometimes over an extended period of time. There is, therefore, a further need for electrodes for such devices that indicate connection quality without any explicit action by the medical device, so that an electrode can be used with various types of devices. With respect to electrodes intended to be applied by a patient rather than a medical professional, e.g., for home health monitoring, there is a continuing need for an indicator of connection quality that does not require specialized training to interpret. There is a corresponding need for an indicator of connection quality that does not require additional devices, circuitry, or hardware outside the electrode for full functionality.

According to an aspect of the present invention, there is provided an electrode having first and second electrical contacts adapted to contact the skin of a subject; a charge-holding structure electrically connected between the first and second electrical contacts; and an indicator coupled to the charge-holding structure so that the indicator changes state in response to a change in the charge stored in the charge-holding structure.

According to another aspect of the present invention, there is provided an electrode having first and second electrical contacts; a rectifier electrically connected between the first and second contacts; a first electrical terminal electrically connected to the first electrical contact; a charge-holding structure electrically connected between the first and second electrical contacts; and an indicator coupled to the charge-holding structure so that the indicator changes state in response to a change in the charge stored in the charge-holding structure.

According to another aspect of the present invention, there is provided a container adapted to retain one or more skin-contact electrodes, the container having an electrical supply having first and second terminals; and a plurality of receptacles for respective ones of the skin-contact electrodes, each receptacle including respective first and second conductors electrically connected to the first and second terminals, respectively, so that a voltage difference is maintained between the first and second conductors of each receptacle for at least one week.

According to another aspect of the present invention, there is provided a method of making a patient-contact device for a medical sensing system, the method including arranging first and second electrical contacts over a support; electrically connecting a charge-holding structure between the first and second electrical contacts; arranging an indicator over the support, the indicator coupled to the charge-holding structure so that the indicator changes state in response to a change in the charge stored in the charge-holding structure; and charging the charge-holding structure so that the indicator has a first visual appearance.

An advantage that may be realized in the practice of some disclosed embodiments is that electrode contact quality can be determined visually when the electrode is applied, without requiring any special hardware or support from the ECG unit or other medical sensing unit. Various aspects provide electrodes that can be used with a range of ECG units and wires. Various aspects further provide a visual indication, either before application or at the time of application, of whether an electrode has reached the end of its useful life. Various embodiments provide indicators that do not require specialized training to interpret. Various examples are usable by colorblind individuals.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Throughout this disclosure, the terms "top" and "bottom" are exemplary and not limiting. Generally speaking, the term "bottom" will refer to the side of an electrode facing the subject when the electrode is in use.

The following description relates to exemplary embodiments of patient-contact electrodes as well as use thereof in monitoring patient condition using a specific medical sensing apparatus, e.g., by taking electrocardiograms (ECGs). However, it will be readily apparent that the herein described concepts can be used with other apparatus that includes electrodes that are adhered to a patient, such as body temperature patches. Still further and in order to provide a suitable frame of reference with regard to the accompanying drawings, certain terms are used throughout. These terms are not intended to narrow the scope of the concepts detailed herein, including those embodied in the claims unless specifically indicated. In addition and in the following description, some aspects will be described in terms that would ordinarily be implemented as software programs. Those skilled in the art will readily recognize that the equivalent of such software can also be constructed in hardware (hardwired or programmable), firmware, or micro-code. Accordingly, aspects of the present invention may take the form of an entirely hardware embodiment, an entirely software embodiment (including firmware, resident software, or micro-code), or an embodiment combining software and hardware aspects. Software, hardware, and combinations can all generally be referred to herein as a "service," "circuit," "circuitry," "module," or "system." Various aspects can be embodied as systems, methods, or computer program products. Because data manipulation algorithms and systems are well known, the present description will be directed in particular to algorithms and systems forming part of, or cooperating more directly with, systems and methods described herein. Other aspects of such algorithms and systems, and hardware or software for producing and otherwise processing signals or data involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

Figure 10:
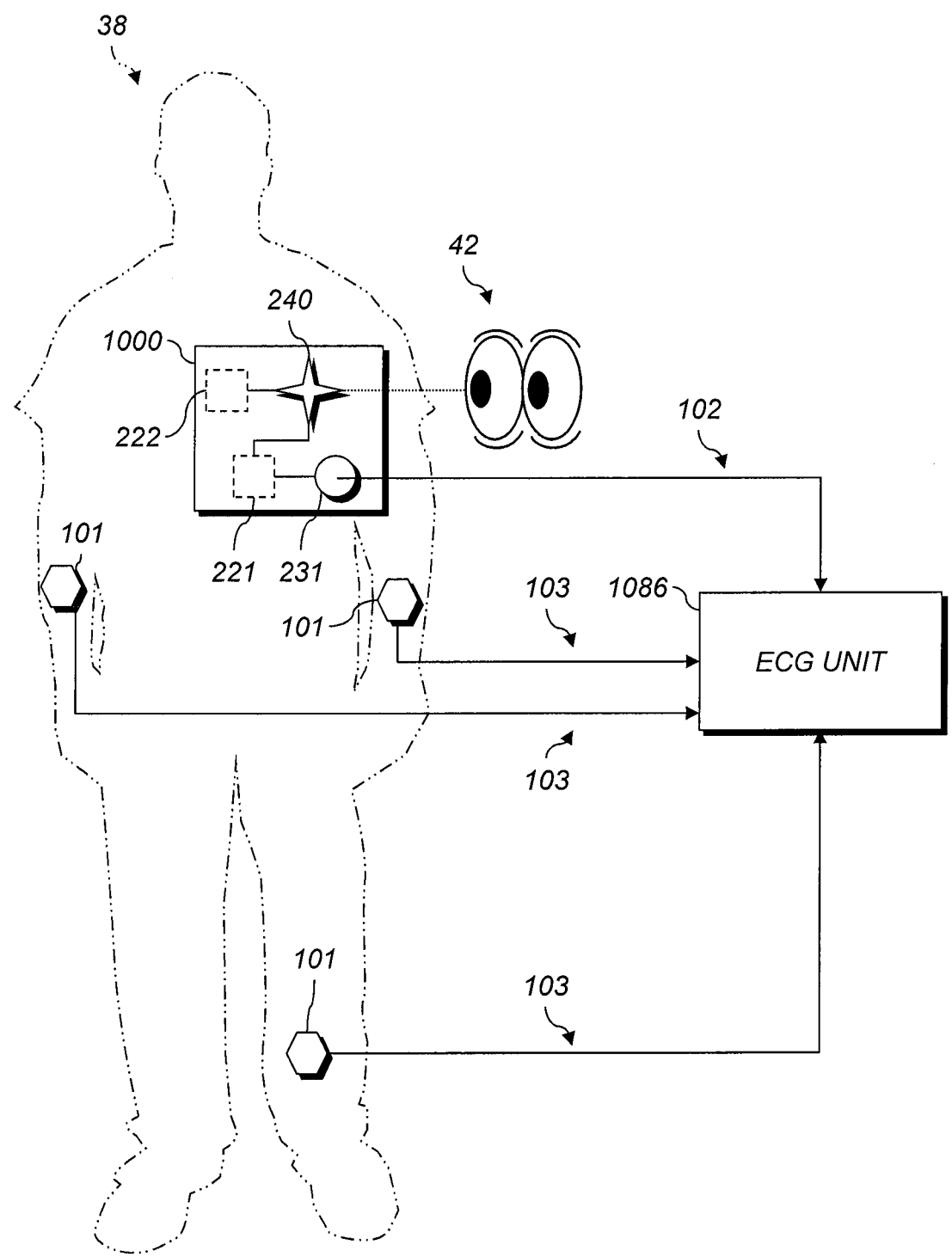
FIG. 10 is a partially-schematic view of an ECG measurement system using an inventive electrode.

FIG. 10 is a partially-schematic view of an ECG measurement system using an inventive patient-contact electrode 1000. Various embodiments of electrode 1000 are shown in FIGS. 2-6. Subject 38 (patient) is shown in phantom for purposes of orientation. ECG unit 1086 receives ECG signals via wires 102, 103 from electrodes 1000, 101. ECG unit 1086 then computes differences between voltages on different electrodes and presents the resulting data to operator 42. ECG unit 1086 can include a microprocessor, microcontroller, FPGA, or other logic device that can perform these functions.

Instructions to cause ECG unit 1086 and other controllers herein (e.g., controller 986, FIG. 9) to perform functions described herein can be stored on one or more tangible non-transitory computer-readable storage medium(s). A "tangible non-transitory computer-readable storage medium" as used herein refers to any non-transitory device or article of manufacture that participates in storing instructions which may be provided to a processor for execution. Such a non-transitory medium can be non-volatile or volatile. Examples of non-volatile media include floppy disks, flexible disks, or other portable computer diskettes, hard disks, magnetic tape or other magnetic media, Compact Discs and compact-disc read-only memory (CD-ROM), DVDs, BLU-RAY disks, HD-DVD disks, other optical storage media, Flash memories, read-only memories (ROM), and erasable programmable read-only memories (EPROM or EEPROM). Examples of volatile media include dynamic memory, such as registers and random access memories (RAM). Storage media can store data electronically, magnetically, optically, chemically, mechanically, or otherwise, and can include electronic, magnetic, optical, electromagnetic, infrared, or semiconductor components.

Electrodes 101 are shown for purposes of an exemplary embodiment on subject 38's left leg, left arm, and right arm. These electrodes 101 can transduce standard electrocardiographic voltage signals LL, LA, and RA, respectively. This permits computing three standard voltage differences I, II, III used in electrocardiography:

$$I=LA-RA$$

$$II=LL-RA$$

$$III=LL-LA.$$

In these three voltage differences, over time, various of the P, Q, R, S, T features of the electrical waves that pass through the heart on each beat can be observed, as is known in electrocardiography. Further details of heart electrical waves are provided in U.S. Pat. No. 7,907,995B2 to Shinya et al., incorporated herein by reference.

Electrode 1000 is shown on patient 38's chest. However, any number of electrodes configured as electrode 1000 can be used, and in any locations on the body of subject 38. Electrode 1000 includes terminal 231 to which wire 102 is connected. Terminal 231 is electrically connected to first contact 221, which makes contact with the skin of subject 38. Second contact 222 is separate from first contact 221 and also makes contact with the skin of subject 38 when electrode 1000 is applied to subject 38 and makes sufficient electrical contact.

Electrode 1000 includes an indicator 240 operatively connected between first contact 221 and second contact 222. As discussed below, the indicator 240 changes state visually, e.g., when the first contact 221 and the second contact 222 are shorted together by the skin of subject 38. Accordingly, in some examples, the first contact 221 and the second contact 222 are adapted to concurrently contact the skin of subject 38 Operator 42 (shown for purposes of orientation) can view indicator 240 to visually determine the quality of the electrode contact, as discussed below. Indicator 240 can thus show the operator 42 whether sufficient contact is made as electrode 1000 is being applied to the subject 38. In various aspects, no specialized test equipment is required, and no confusion of wires will occur since electrode 1000, via the indicator 240, indicates the quality of its own contact with subject 38. In various embodiments, the indicator 240 includes an electronic ink (e-ink) display element, e.g., an electrochromic display element. An example of an electrochromic display element is discussed below with reference to FIG. 7.

Figure 1:
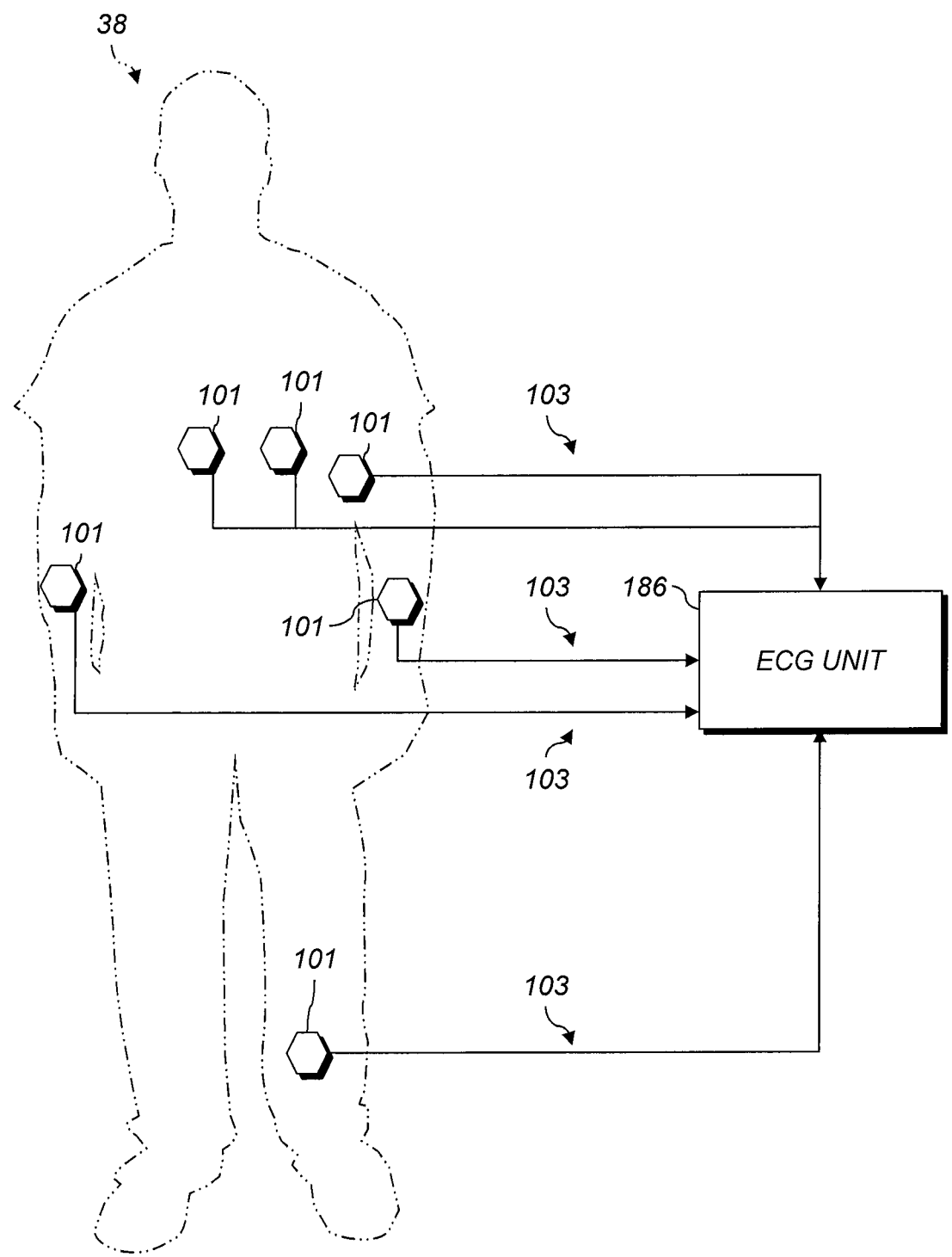
FIG. 1 is a partially-schematic view of a conventional electrocardiogram (ECG) measurement system.
Figure 2:
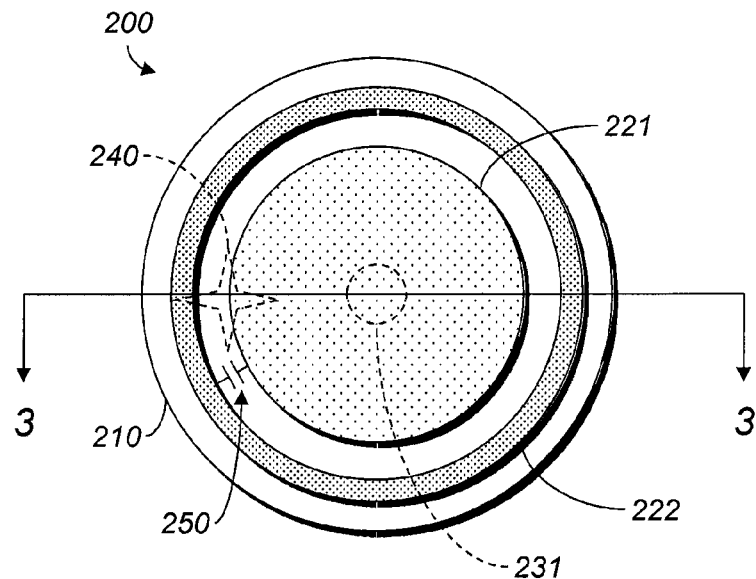
FIG. 2 is a bottom plan view of an electrode according to various aspects.

FIG. 2 is a bottom plan view of a skin-contact biopotential electrode (SCBE) electrode 200 according to various aspects. This electrode is an example of electrode 1000 shown in FIG. 10 and can be, e.g., an electrocardiogram patient-contact electrode. Electrode 200 is formed on or around support 210, e.g., a plastic film. Support 210 is preferably electrically insulating. Terminal 231 protrudes from the top of the electrode 200 so that it can be contacted by, e.g., pressing a snap-fit receptacle on a wire 102 (FIG. 10) over the terminal 231. Illustrated is a subject side of electrode 200. In some examples, e.g., as discussed below with reference to FIGS. 3 and 4, at least a portion of support 210 spaces the electrical terminal 231 apart from the illustrated subject side of the support 210.

Separate first and second electrical contacts 221, 222 are adapted to contact the skin of a subject. The subject can be a person or an animal. Shaving any hair off the area of the subject to be contacted before applying electrode 200 can improve performance. By "separate" it is meant that no low-resistance DC current path exists between the contacts 221, 222 when the electrode is not attached to a subject. Contacts 221 and 222 are preferably separated by at least 1MΩ at DC, although parasitic capacitances may provide AC paths between the contacts 221, 222. Each of the contacts 221, 222 can include metal, gel (e.g., electrolyte gel), hydrogel, conductive adhesive, or a metal or metal salt. In the example shown, the first electrical contact 221 is a disk of a desired thickness and radius. The second electrical contact 222 is an annulus of a desired thickness, inner radius, and outer radius surrounding the first electrical contact in the plane of the support 210. The first and second contacts 221, 222 are shaded differently for clarity; they can have the same construction or be constructed differently.

Electrical terminal 231 is electrically connected to the first electrical contact 221. The terminal 231 can be, e.g., a snap or tab. The first electrical contact 221 can be the contact or the main contact with which ECG signals are measured.

A charge-holding structure 250 is electrically connected between the first and second electrical contacts 221, 222. As shown in the example of FIG. 2, the charge-holding structure 250 of the electrode 200 is connected in series between the first and second electrical contacts 221, 222. The charge-holding structure 250 is represented graphically as a capacitor, but does not have to be a capacitor. The charge-holding structure 250 can be a separate element, or can be a property or component of another structure in the electrode 200, e.g., a parasitic capacitance between the contacts 221, 222. Various examples are discussed below. In this disclosure, references to a "charged electrode" refer to an electrode with a charge-holding structure 250 that is holding a nonzero amount of charge, with any other details on the amount of charge as specified by the context.

At least one indicator 240 is coupled, by arrangement or otherwise, to the charge-holding structure 250. The indicator 240 changes state in response to a change in the charge stored in the charge-holding structure. The state change can be a visible change, and "visible" can include human-visible or, if operator 42 is a robot or other automated system, machine-detectable. Machine-detectable changes can be, e.g., changes visible at a wavelength of electromagnetic radiation to which a camera on a robot is sensitive. For example, indicator 240 can be e-ink, as discussed above.

Since charge-holding structure 250 is electrically connected to the contacts 221, 222, changes in the potential or impedance between the contacts 221, 222 can change the charge held in the structure 250. When electrode 200 is applied to a subject, if both contacts 221 and 222 make sufficient contact with the subject's skin, the skin will serve as a resistive connection between contacts 221, 222. Therefore, charge in the charge-holding structure 250 will dissipate through the skin. If only one of the contacts 221, 222 is electrically connected to the subject's skin, that resistive connection will not be made and charge will be held in the charge-holding structure 250 (in the absence of other current paths between the contacts 221, 222). That is, in this and other examples, the charge-holding structure 250 is configured to, in response to an electrical connection between the first electrical contact 221 and the second electrical contact 222 through the subject 38 (e.g., the subject's skin or a skin surface of the object), dissipate at least some of the charge stored in the charge-holding structure through the subject 38. To summarize, sufficient contact of both contacts 221, 222 causes a change in charge in the structure 250, and thus causes a change in the visual appearance of indicator 240. In this example, when the electrode 200 is applied to the subject, if the indicator 240 changes visibly, the electrode has been successfully applied to the subject, and the conductor, e.g., gel, is functioning. If the indicator 240 does not change visibly, application was not successful. This can be due to lack of skin contact (e.g., from grease, hair, not enough application pressure) or degradation of the electrode (e.g., drying out of conductive gel). In an example, the ANSI-AAMI Ec11 standard provides a model for electrode to skin impedance. This model is a 0.62MΩ resistor in parallel with a 4.7 nF capacitor. When contacts 221, 222 are electrically connected to the skin, the charge in charge-holding structure 250 will dissipate through the 1.24MΩ (at DC; plus resistance within the subject's body) series connection of the contact 221-skin interface and the skin-contact 222 interface.

In an embodiment, the indicator 240 visibly shows a first indication, e.g., "APPLY" or "ADHERE", or an icon when the charge-holding structure 250 is holding a first selected charge, or more. Throughout this disclosure, unless explicitly noted, references to a particular charge can be to the magnitude of that charge only, or to the sign and magnitude of that charge, as desired. The indicator 240 hides the first indication from view when the charge-holding structure is holding a second selected charge or less. The first and second charges can be the same or different. The charge-holding structure 250 can, but does not have to, be fully charged or fully discharged for the indicator 240 to change state. For example, the charge-holding structure 250 can be charged before the electrode is to be used. The first indication thus appears. When the electrode is successfully applied, the structure 250 discharges and the first indication disappears. In this example, the first selected charge has higher magnitude than the selected second charge.

In another example, the first selected charge has lower magnitude than the second selected charge. The first indication is hidden when the structure 250 is holding the first selected charge or less, and shown when the structure 250 is holding the second selected charge or more. In this way, a charged electrode 200 has no visible indication. When the electrode 200 is applied correctly, the indicator 240 visibly shows the first indication (e.g., "OK" or "COUPLED", or an icon).

In another example, the indicator 240 is adapted to visibly show a first indication when the charge-holding structure is holding a first selected charge (or more, or less) and to visibly show a second indication different from the first indication when the charge-holding structure is holding a second selected charge (or less, or more). Instead of hiding and showing a single indication, the indicator 240 can change indications when the electrode 200 makes sufficient contact with the subject's skin, e.g., by changing from "NOT READY" to "READY." In another example, the first or second indications are different intensity levels of a given pattern.

Many conventional ECG systems use color coding to indicate which wires should be connected to which electrodes, and to permit operators to identify specific electrodes by the wires to which they are attached. However, partly- or wholly-colorblind individuals may have difficulty distinguishing the wires by color. In at least one embodiment, the visual appearance of indicator 240 in either state (e.g., charged or not) is substantially monochromatic. This permits colorblind individuals to readily identify expired electrodes, or electrodes with poor contact.

In addition, whether an operator is colorblind or not, display screens often are not color matched to inks on plastic cable sheaths. Presenting indications directly on the electrodes advantageously removes possible error that could be introduced if an operator looked at an indication on the screen of an ECG unit and mis-identified the color code being represented. For example, looking at a purple trace on screen and thinking it corresponded to a dark-blue-coded wire could result in confusion. Presenting indications directly on the electrodes removes this possible source of error. This is particularly useful because the human brain is known to have poor color memory. Identifying matching colors without being able to compare them within the same field of view, e.g., 2° or 10°, can be very difficult. This factor could limit operator performance in situations in which the operator looks at the ECG-unit screen, and then has to walk several paces to the subject. Presenting indications on the electrodes obviates this problem.

Figure 3:
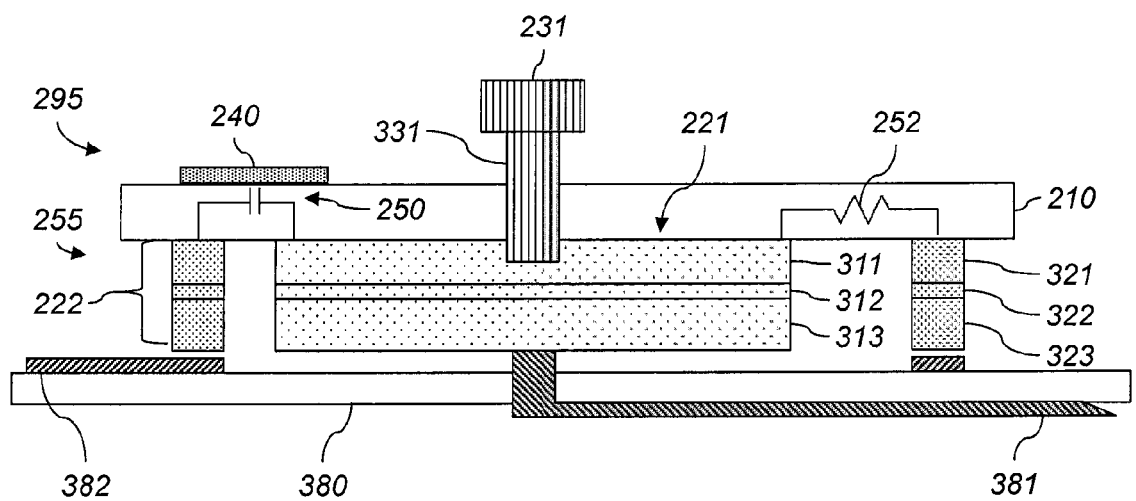
FIG. 3 is a cross-section along line 3-3 in FIG. 2.

FIG. 3 is a cross-section along line 3-3 in FIG. 2. The support 210, e.g., MYLAR or KAPTON, has a subject side 255 and an opposed non-subject side 295. The subject side 255 and the non-subject side 295 do not have to be flat or smooth. The subject side 255 can generally have normal(s) pointing more towards than away from subject 38 when the electrode is applied to the subject 38, and the non-subject side can generally have normal(s) pointing more away from than towards subject 38 when applied. Accordingly, when electrode 200 is removably attached to a skin surface of a subject 38, the subject side 225 can be oriented generally facing the subject 38. In an example, more than 50% of the subject side 255 is hidden from the operator when the electrode 200 is applied to the subject 38, and at least 75% of the non-subject side 295 is not hidden from the operator when the electrode 200 is applied. Charge-holding structure 250 is represented as being embedded in support 250 and the indicator 240 is represented as being disposed over non-subject side 295. In the illustrated example, the indicator 240 is arranged so that at least a portion of the support 210 spaces the indicator 240 away from the subject side 255 of the support 210, as shown. Other configurations can also be used; the structure 250 and the indicator 240 can each be wholly or partly embedded in the support 210, or disposed over or on either side thereof.

In this example, terminal 231 is disposed over the non-subject side 295. Via 331, e.g., a plated through-hole or press-fit metal post, electrically connects terminal 231 to contact 221. As discussed above, contact 222 is not electrically connected to terminal 231 at DC except, possibly, through the skin of a subject or parasitics (e.g., non-∞ DC resistance of the support 210).

In an example, each contact 221, 222 includes a multi-layer structure. Conductive layers 311, 321 (respectively) are, e.g., silver (Ag) or another metal. Stabilizing layers 312, 322, respectively, are, e.g., silver chloride (AgCl) or another metal. Stabilizing layers can reduce the chemical reactivity (e.g., solubility) of conductive layers 311, 321. Gel layers 313, 323, respectively, include, e.g., conductive adhesive to adhere the electrode to the skin of the subject. The conductive adhesive can be a hydrogel and can be die-cut to the desired shape before applying to support 210.

In various aspects, electrode 200 includes a release liner 380. Release liner 380 is designed to peel off gel layers 313, 323 without damaging the gel layers, thus permitting simpler handling of electrode 200 before the time to apply it. Release liner 380 has electrical terminals 381, 382 electrically connected to the first and second electrical contacts 221, 222, respectively. In this example, electrical terminals 381, 382 are electrically connected to gel layers 313, 323, respectively. Electrical terminals 381, 382 can extend towards the periphery of release liner 380, e.g., as shown, to provide points that can be readily gripped or electrically contacted to interact electrically with the indicator 240. An example of a release liner used in this way is discussed below with reference to FIG. 8.

In at least one embodiment, a charge-transport unit 252 is electrically connected between the first and second electrical contacts 221, 222. In the example shown, charge-transport unit 252 is a resistor, e.g., 100MΩ. Charge-transport unit 252 can be another active or passive component, e.g., a photodiode. The charge-transport unit 252 slowly discharges charge-holding structure 250, e.g., so that the structure 250 will be discharged when the gel layers 313, 323 are dried out and at the end of their useful life. The remarks above about high DC impedance between contacts 221, 222 apply here, but the DC impedance is deliberately reduced by introducing charge-transport unit 252.

Figure 4:
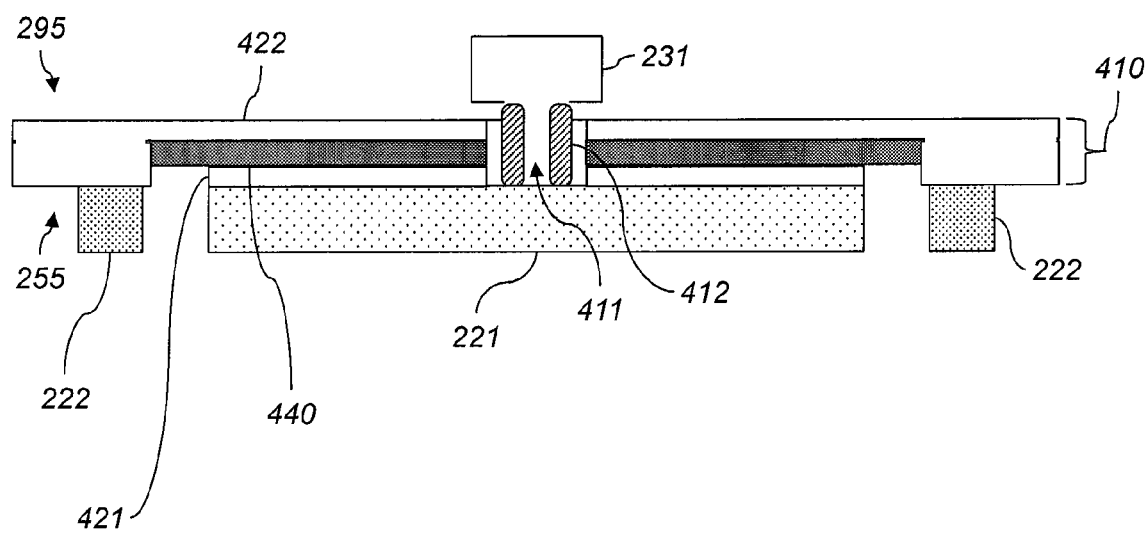
FIG. 4 is a cross-section of an electrode according to various aspects.

FIG. 4 is a cross-section of an electrode according to various aspects. This electrode is an example of electrode 1000 shown in FIG. 10. This cross-section is through the center of a round electrode, similar to line 3-3 on FIG. 2, but with indicator 440 structured differently. Support 410 has via 411 (e.g., a through hole) carrying conductive adhesive 412 (shown hatched) to connect terminal 231 to first contact 221. First contact 221 is also connected to a first conductor 421. Second contact 222 is connected to second conductor 422, which is separate and spaced apart from first conductor 421. The indicator 440 includes an electronic ink controlled by the charge between the first and second conductors 421, 422. In this example, the electronic ink of indicator 440 is arranged between the first and second conductors 421, 422. Indicator 440 can also be arranged over one of the two conductors 421, 422 or in other mechanical configurations.

In at least one embodiment, the support 410 contains the electronic ink. For example, the support 410 can be a plastic or glass matrix with embedded e-ink microbeads. In the example shown, the support 410 is defined by a subject side 255 and opposed non-subject side 295. The first and second electrical contacts 221, 222 are arranged over the subject side 255 of the support 410. Accordingly, as shown in the illustrated example, at least a portion of the support 410 spaces the first and second electrical contacts 221, 222 apart from the non-subject side 295. The first conductor 421 is also disposed over the subject side. In other examples, the first conductor 421 is disposed over the non-subject side 295.

In the example shown, the second conductor 422 is arranged partly over the subject side 255 and partly over the non-subject side 295. Second conductor 422 can be, e.g., a foil wrapped around support 410 from non-subject side 295 to subject side 255. Second conductor 422 can also include electrically-connected respective portions on sides 295, 255. In this and other examples, e.g., those shown in FIGS. 5 and 6 the first conductor 421 and the second conductor 422 can be disposed at least partly in or on the support. In the Illustrated examples, the first conductor 421 is spaced apart from the non-subject side 295 by at least part of the support 410. In the illustrated example, at least part of the second conductor 422 is spaced apart from the subject side 255 by at least part of the support 410.

Figure 5:
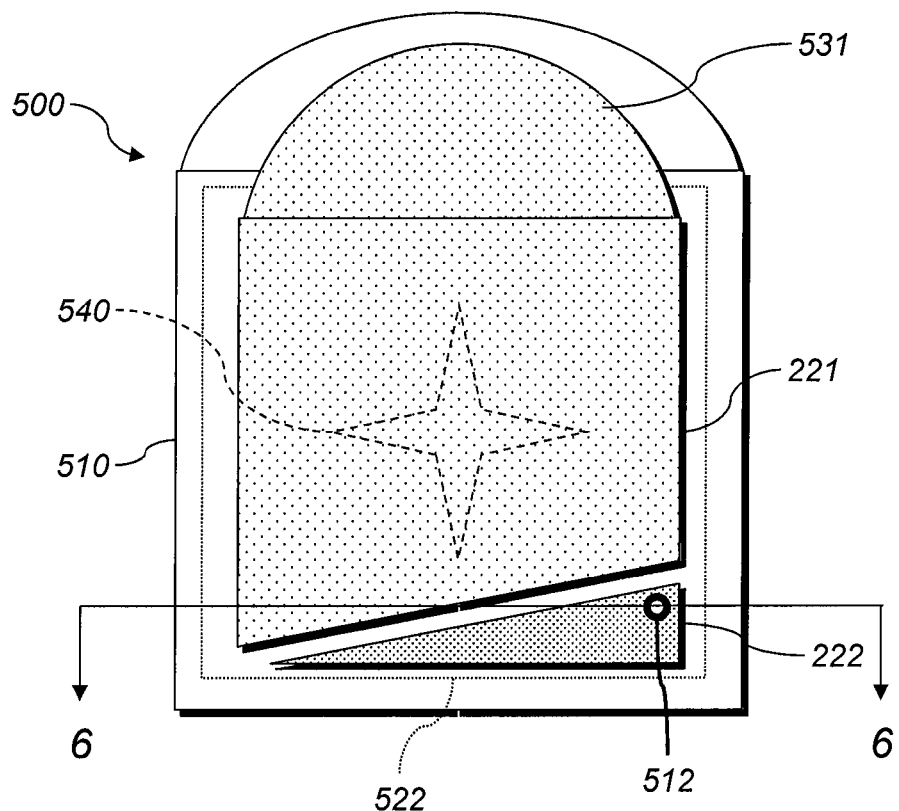
FIG. 5 is a bottom plan view of an electrode according to various aspects.

FIG. 5 is a bottom plan view of an electrode 500 according to various aspects. This electrode 500 is an example of electrode 1000 shown in FIG. 10. The electrode 500 has a flat terminal 531 that can be contacted by, e.g., gripping it with an alligator clip. The terminal 531 can be arranged over the subject side of the electrode 500, or can wrap around or punch through support 510 to the non-subject side of the electrode 500. Electrode 500 has support 510. In this example, the charge-holding structure includes the electrical conductor 522 spaced apart from the first electrical contact 221 and electrically connected to the second electrical contact 222 by via 512. The indicator 540 includes an electronic ink controlled by the charge between the first electrical contact 221 and the electrical conductor 522. In this way, a separate electrical conductor connected to first contact 221 is not required, since first contact 221 itself forms, e.g., one plate of a parallel-plate capacitor. This configuration can also be used with round electrodes (e.g., FIG. 2) or any other shape.

In at least one embodiment, the area of the second electrical contact 222 is less than the area of the first electrical contact 221. The area of the first electrical contact 221, which is connected to terminal 531, can be selected to match the area of a conventional ECG electrode to maintain similar measurement impedance as conventional electrodes, advantageously making these inventive electrodes drop-in replacements for conventional electrodes. In at least one embodiment, the first and second electrical contacts are positioned so that neither surrounds the other. For example, one side, or as shown, one corner can be occupied by the second contact 522. As used herein, references to "position" include "shape" and "size," unless otherwise indicated. That is, the relative position, shape, size, or any combination of these can be selected so provide a contact design in which neither contact 221, 222 surrounds the other 222, 221.

Figure 6:
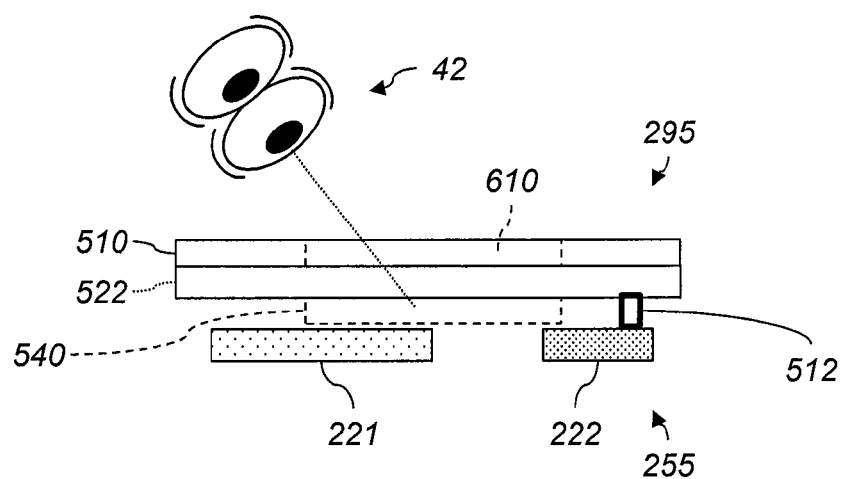
FIG. 6 is a cross-section along line 6-6 in FIG. 5.

FIG. 6 is a cross-section along line 6-6 in FIG. 5. Since this section line does not pass through indicator 540, hidden lines are shown to indicate features related to indicator 540. Subject side 255 and non-subject 295 of support 510 are as shown. Support 510 can include a plastic film. The first and second electrical contacts 221, 222 are disposed over the subject side 255 of the support 510.

In various aspects, the second conductor 522 is arranged over the non-subject side 295. Via 512 through the support 510 electrically connects the second conductor 222 to the second electrical contact 522. Via 512 can be any via, through-hole, or other conductive path through a layer including the indicator 540. The second conductor 522 can be a transparent conductive electrode or include apertures or other features to permit light reflecting off indicator 540 to pass through to the operator 42.

In this example, the indicator 540 is on the subject side 255 of the support 510. Some supports 510 are opaque, e.g., metal film. Others significantly affect the appearance of objects viewed through them, e.g., KAPTON. In some aspects, an aperture 610 is defined in the non-subject side 295 of the support 510 so that the indicator 540 is visible to operator 42 through the aperture 610. The aperture 610 can be provided by die-cutting or laser-scribing the support 510; by assembling support 510 of separate pieces to leave a space between the pieces; or by forming the support 510 of clear material or inlaying it with clear material.

Figure 7:
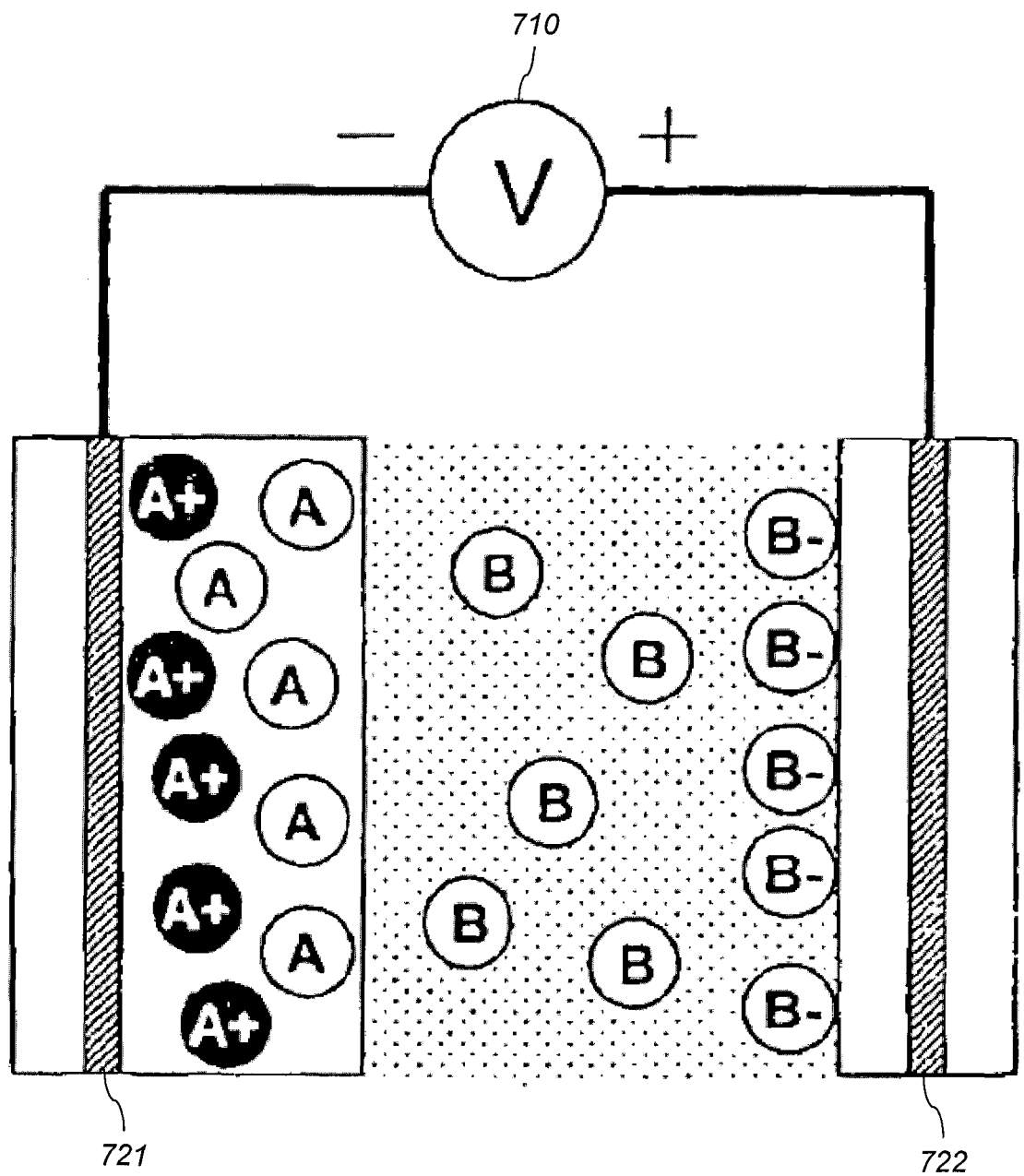
FIG. 7 is a schematic showing operation of an electrochromic display according to various aspects.

FIG. 7 is a schematic showing operation of an electrochromic display according to various aspects. This display is an example of indicator 240 shown in FIG. 10. Further information is given in U.S. Publication No. 2007/0002007, incorporated herein by reference.

FIG. 7 shows a nanostructure type of electrochromic display. This type of display exhibits non-volatility and is capable of rapid color change. This is achieved by attaching a suitable molecule, one that is colorless in the oxidized state and colored in the reduced state, onto the surface of a monolayer of colorless semiconductor on a transparent electrode formed on glass or another substrate (e.g., MYLAR). Voltage source 710 applies potential between electrodes 721, 722. When a sufficiently negative potential is applied at one electrode (e.g., electrode 721), with the other electrode 722 held at ground potential, electrons are injected into the conduction band of the semiconductor and reduce the adsorbed molecules (the coloration process). The reverse process occurs when a positive potential is applied at the electrode 721 and the molecules become bleached (transparent). In FIG. 7, species A and A+ are in different color states. Upon application of a negative voltage to electrode 721 with respect to electrode 722, as shown, species A (which can, e.g., be a viologen), which is adsorbed within the nanostructure, becomes A+. Electrons are transferred to species B in the electrolyte to form B− ions, which then migrate towards the positive terminal (electrode 722). When power supply is disconnected, it takes a long time for B− ions to reach A+ before a reverse charge transfer can take place. Indeed, it is common for such devices to retain their color change for the order of days.

This system combines the relative immobility of an electrochromic material with the rapidity and coloration efficiency of molecular systems. Because a single molecular monolayer does not absorb a perceptible amount of light, nanocrystalline semiconductor films are used to promote the light absorption property of the molecular monolayer to visible color changes. The nanocrystalline layer is highly porous to encourage more molecular monolayer to be present. As light passes through the layer, it crosses several hundreds of monolayers of colored molecules, giving a strong absorption.

Figure 12:
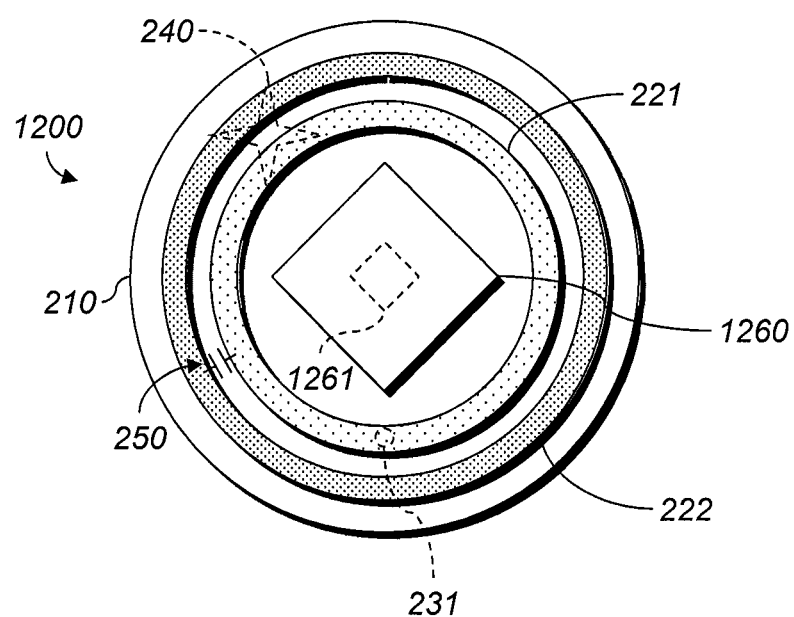
FIG. 12 shows an electrode according to various aspects. The attached drawings are for purposes of illustration and are not necessarily to scale, in each dimension individually or in any set of dimensions together.

FIG. 12 shows an electrode 1200 according to various aspects. Circle and diamond shapes are shown for clarity, but are not limiting. In these aspects, electrical connection between first and second contacts 221, 222, as indicated by indicator 240, is a measure of whether the electrode 1200 was properly applied. When the electrode 1200 is properly applied, indicator 240 changes state. This is used as a surrogate for an indication of effective contact between a non-biopotential sensor 1260 and the skin of subject 38 (FIG. 10). A "non-biopotential" sensor is a sensor designed to measure a property, e.g., of the subject or the subject's environment, other than a potential at the skin of the subject. As in FIG. 2, over support 210 are arranged first and second contacts 221, 222, with indicator 240 and charge-holding structure 250 connected between them. Terminal 231 can be connected to contact 221, or terminal 231 can be omitted. Charge is dissipated through the skin when good electrical contact is achieved. First and second contacts 221, 222 are arranged with respect to sensor 1260 so that the probability is high that if effective electrical contact between contacts 221, 222 and the skin is present, effective contact (e.g., thermal) between sensor 1260 and the skin is also present. Not all sensors 1260 require physical skin contact. For example, sensor 1260 and electrode 1200 can be arranged so that, when first and second contacts 221, 222 are electrically connected through the patient's skin, sensor 1260 is spaced apart from the skin by a selected amount or less, e.g., 1 mm or less.

Non-biopotential sensor 1260 can be, e.g., a temperature sensor adapted to sense the temperature of the skin of the subject when the electrode is applied to the skin of the subject. Output interface 1261 provides information sensed by the non-biopotential sensor. For example, output interface 1261 can include an infrared (IR) "target," i.e., IR emitter, or a wireless-networking transmitter. Examples of non-biopotential sensors are described in U.S. Pat. Nos. 8,079,756 and 7,857,507, incorporated herein by reference. In at least one embodiment, electrode 1200 has an IR target as interface 1261 and is adapted to be placed proximate to the surface of a subject. Electrode 1200 can include an insulator for protecting the target from exterior, ambient IR, and can include bar codes or other indicia uniquely associated with either the electrode 1200 (e.g., a serial number) or the subject (e.g., a subject or patient ID number). Electrode 1200 can also include a thermometer (not shown) for sensing the level of IR radiation from the IR target (interface 1261) and can include a display unit (not shown) that displays the temperature associated with such a level. Interface 1261 can also include a transmitter for wirelessly communicating information about such level to a remote location.

In various aspects, non-biopotential sensor 1260 can include a bio-reactive agent for indicating characteristics such as the pH of the subject's skin. In an example, output interface 1261 can include a piece of litmus or other paper that changes to one of two or more colors, depending upon the pH of the liquid or other material in which the bio-reactive agent is in contact. The bio-reactive agent can be sensitive to, and altered by, liquid or gas effluents from the subject's skin, such as perspiration. The bio-chemical components of such effluents can be indicative of certain health or medical conditions of the subject, e.g., blood glucose levels, jaundice, lead contamination, turgor, infections, or anemia. In another example, sensor 1260 can include a color changing bio-reactive agent, and output interface 1261 can include a window in support 210 through which the color of the bio-reactive agent can be detected by spectroscopy, which involves an analysis of the spectral distribution of a known light source after being reflected from the surface of the bio-reactive agent.

In various aspects, an electrochromic module can include an electrochromic icon (an indicator 240, FIG. 2) electrically connected to two conductors. The module can be packaged in a MYLAR package. The conductors can be electrically connected to contacts 221, 222 (FIG. 2), respectively. Voltage can be applied across conductors to cause the icon to appear. In an example, applying 0.5 VDC across the conductors can cause the icon to become visible at a certain contrast (visibility) and applying 1.5 VDC across the conductors, e.g., from a conventional consumer alkaline battery, can cause the icon to become visible more darkly than at 0.5 VDC. After charging, the conductors can be electrically connected, e.g., by a metal shorting bar or by human skin. The latter can occur when an electrode incorporating the display module is applied to the skin of a subject. Electrically connecting the conductors of the electrochromic module can cause the electrochromic icon to disappear.

The MYLAR or other package of an electrochromic module can be used directly as a support 210 (FIG. 2) for an electrode, e.g., a biopotential electrode. Alternatively, the conductors of the module can be shaped, positioned, or oriented to electrically connect to contacts 221, 222. For example, if the conductors of the module are accessible on the same side as the electrochromic icon, they can be folded under and the module can be layered on top of a support for contacts 221, 222.

Figure 8:
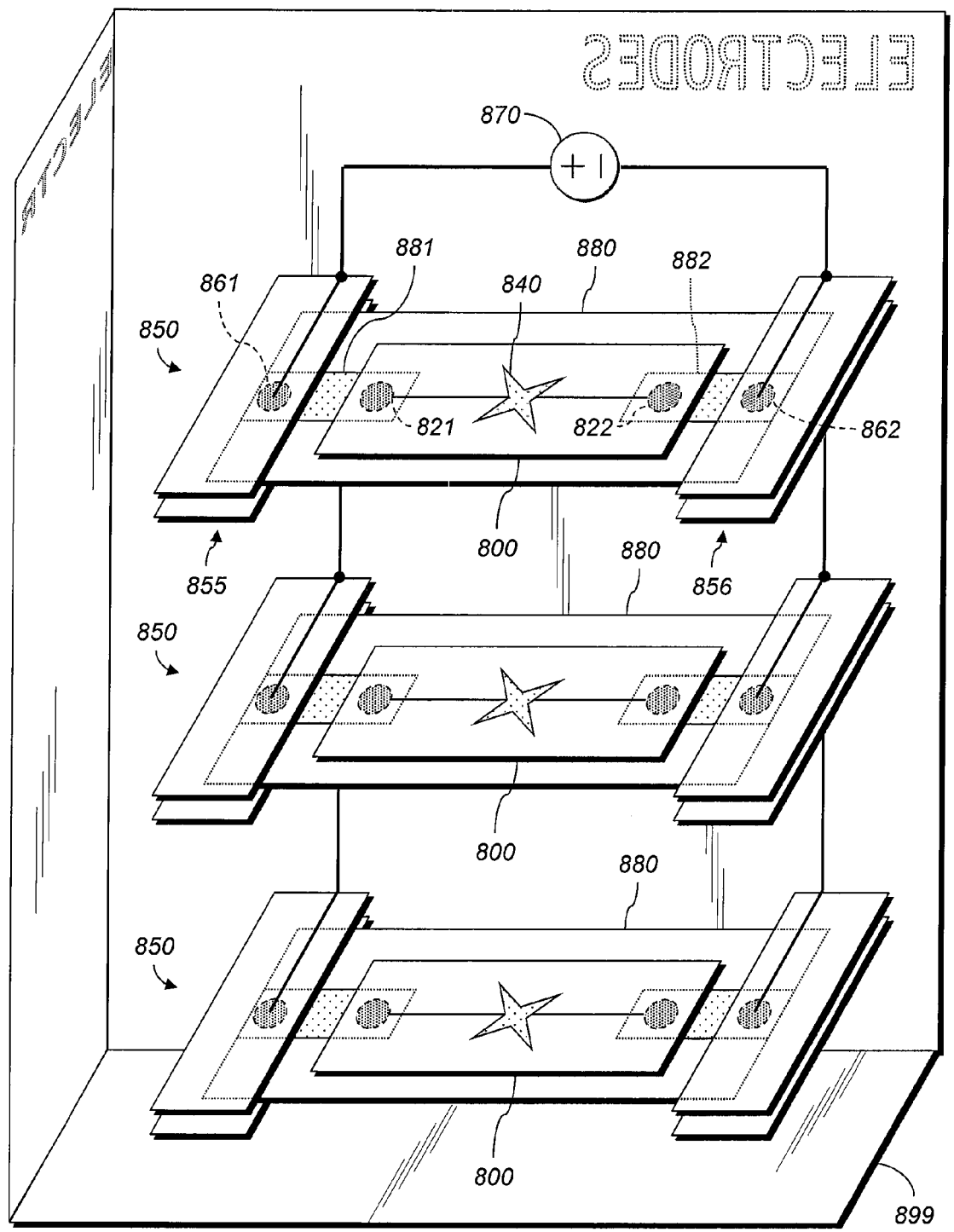
FIG. 8 is a perspective of a container for skin-contact biopotential electrodes.

FIG. 8 is a partially-schematic perspective of a container 899 that retains skin-contact biopotential electrodes, e.g., electrocardiogram (ECG) patient-contact electrodes, until they are removed from container 899 to be removed for use. This figure shows the interior of container 899; the front, top, and left sides are omitted from the figure to more clearly show the internal structure of the container. Container 899 is labeled "ELECTRODES" on the outside. Three biopotential electrodes 800 are shown, each with indicator 840 electrically connected to contacts 821, 822. (For clarity, not all reference numbers are shown on the middle or bottom electrodes 800). Each electrode 800 is mounted on a release liner (removable backer sheet) 880 with conductors 881, 882 electrically connected to contacts 821, 822, respectively. Receptacle 850 includes a pair of rails 855, 856 on each side to retain release liner 880. Single rails can also be used as long as the container will not be tipped over, or if the single rails are adhesive or include other mechanical retention features. Receptacle 850 also has conductors 861, 862 connected to conductors 881, 882. Conductors 861, 862 for each receptacle 850 are electrically connected, as shown. Electrical supply 870, e.g., a battery, has two terminals (electrically connected to conductors 861, 862, respectively). Electrical supply 870 is represented graphically as a voltage source and can be a voltage, current, or charge (E-field) source, battery- or mains-powered. Electrical supply 870 maintains a voltage difference between the first and second conductors 861, 862 for at least one week, or at least one month, or at least six months, or at least one year. The voltage difference can be maintained directly, by sourcing voltage, or indirectly, e.g., by sourcing current. The voltage difference can droop over time, e.g., if the electrical supply is a battery.

In this example, the receptacles 850 mechanically retain release liners 880 of the skin-contact biopotential electrodes 800. In other examples, release liners 880 are not used. In at least one embodiment, the first or the second conductor 861, 862, or both, is adapted to make electrical contact with a conductive hydrogel and to be mechanically separable from the conductive hydrogel without damaging the conductive hydrogel. First and second conductors 861, 862 can be TEFLON-coated so they do not stick.

Figure 9:
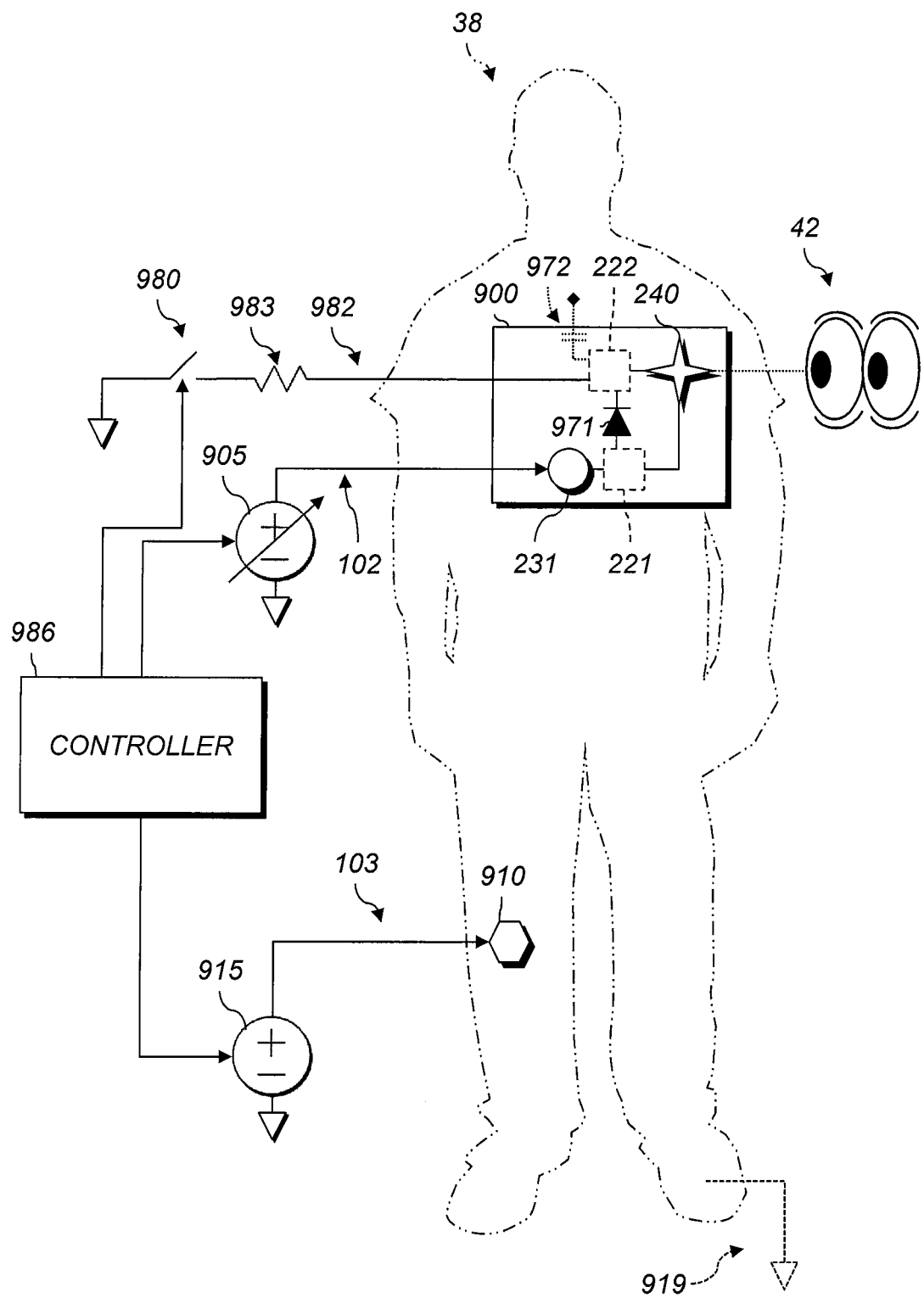
FIG. 9 is a schematic of a system for testing the contact quality of an ECG electrode.

FIG. 9 is a schematic of electrode 900, and a system for testing the contact quality of electrode 900. This system can be used to test contact quality immediately after an electrode has been applied, or some time after the electrode has been applied. For example, in continuous-monitoring applications (as opposed to diagnostic applications), ECG electrodes such as electrode 900 can remain attached to a patient for several days or more. This system can be used to test contact quality, e.g., each day.

Biopotential electrode 900 includes rectifier 971, e.g., a diode or field-effect transistor (FET), electrically connected between the first and second electrical contacts 221, 222. Rectifier 971 can include one or more elements (e.g., diode(s)) in parallel; those elements can be through-hole, surface-mounted, or another packaging style. The rectifier 971 can be electrically connected so that its forward-conduction direction is from the first electrical contact 221 to the second electrical contact 222, as shown. The rectifier 971 can also be connected in the other direction. Roles of contacts 221, 222, and directions of current flow, can be interchanged.

In various aspects, the electrode 900 is configured for application to the skin of the subject 38. The second electrical contact 222 is positioned (or shaped or sized, as discussed above) so that the second electrical contact has a capacitive electrical connection with the subject in at least one of the following situations (this list is not limiting):

1) improper application of the electrode 900 to the skin of subject 38; and 2) partial peeling of the electrode 900 off the skin of subject 38 after proper application.

This capacitive connection is represented graphically as capacitance 972. Its function is discussed further below with reference to the current drain. "Improper" application can include applying the electrode to subject 38's skin with too little pressure so the electrode does not stick well; using too much pressure so conductive gel is squeezed out from between the skin and contacts 221 or 222; adhering only part of the electrode to the skin; adhering the electrode to the skin so that it has a bump or ripple in which the contacts 221 or 222 do not make effective electrical connection with the skin; or wholly or partly trapping a cable, a piece of dirt or foil, or another foreign object between the electrode and the skin so that the electrical connection between contacts 221 or 222 and the skin is higher-impedance, more capacitive, or otherwise less effective than when the electrode is properly applied to the skin.

Time-varying electrical supply 905 (a voltage or current supply) is electrically connected to the terminal 231 to successively supply one or more potential(s) to terminal 231 (and thus to contact 221) through wire 102. A current drain is also included; the term "drain" is used for convenience, and the current drain can either source or sink current depending on the potentials applied to the electrodes. In this example, the current drain includes a second skin-contact biopotential electrode 910 having an electrical contact and a second electrical terminal (not shown; a conventional or inventive electrode can be used). Wire 103 electrically connects the contact and terminal of the electrode 910 to a reference-voltage supply 915 that selectively supplies a reference voltage to electrode 910. The reference-voltage supply 915 can be a strap to an existing voltage rail, e.g., ground, or can supply a particular DC voltage. In another example, the current drain can be ground connection 919 directly to subject 38. For example, is subject 38 is lying on an examination bed and has skin-to-metal contact with a grounded portion of that bed, or if subject 38 is wearing a grounding wrist strap, the current drain is that ground conductor. The current drain can be a grounding, grounded, or neutral conductor, or any conductor that will safely provide a return path for current from the electrical supply 905.

Controller 986 is a control device that directs operation of time-varying electrical supply 905 and reference supply 915. Controller 986 can include a microprocessor or other components describe below with reference to data processing system 110, a 555 timer, or a one-shot (a device that produces a pulse of a specific amplitude, e.g., of voltage, and duration when triggered, independently of the duration of the trigger). Controller 986 causes the time-varying electrical supply 905 to sequentially apply first and second potentials for respective selected lengths of time. In an example, controller 986 causes the time-varying electrical supply 905 to apply a substantially square pulse of the first potential, followed by the second potential. A square pulse can have, e.g., a rise or fall time<10% of the on-time of the pulse.

The first potential from supply 905 (and the reference voltage, if supply 915 is used) will drive the rectifier 971 toward forward bias if the two terminals of the rectifier 971 are electrically separated. This will be the case if the contacts 221, 222 are not shorted together or are not electrically connected by any elements other than the rectifier 971 and the indicator 240. The second potential (and the reference voltage, if used) will drive the rectifier 971 toward reverse bias if the two terminals of the rectifier are electrically separated. As a result, if the first and second electrical contacts 221, 222 are not shorted together (e.g., are separated by more than 10MΩ, when the first and second potentials are sequentially applied, the charge-holding structure 250 (FIG. 2) charges between the electrical supply 905 and the current drain (e.g., supply 915 or ground tie 919) and the indicator 240 changes state. Current out of second electrical contact 222 can flow to or from the current drain via the capacitive connection discussed above and the body of subject 38. For example, a high pulse can charge the node at contact 222, and the low pulse can bring the node at contact 221 low to impress a voltage across the indicator 240. The indicator does not have to have any particular state to begin with. For example, the charge-holding structure does not have to be charged when this procedure is carried out. If reference-voltage supply 915 is used, controller 986 causes the reference-voltage supply 915 to supply the reference voltage while the first and second potentials are applied.

In various aspects, the controller 986 includes a measurement unit (not shown) for measuring respective voltages on the wires 102, 103 when the reference voltage is not applied. The measurement unit produces a difference signal indicating the voltage difference between the respective measured voltages. In this way, the controller 986 can test for sufficient contact of electrode 900 to subject 38, and then can collect ECG measurements of subject 38. In an example sequence of events:

Contact 222 comes loose and is no longer shorted through subject 38's skin to contact 221;

Contact 221 is brought to +5V;

The node at contact 222 charges to −4.3V through the rectifier 271, moving current through a capacitive connection between the contact 222 and the body of subject 38 and out the current drain;

Contact 221 is brought to a voltage lower than the voltage on contact 222 (e.g., 0V). The node at contact 222 is held at a higher voltage than contact 221 (e.g., >0V) by the reverse-biased rectifier 971 and the capacitance divider from contact 221 to contact 222 to subject 38's ohmic connection to ground;

The charge-holding structure 250 charges as charge is drawn out of the node at contact 221 through the wire 102; and The voltage developed across the indicator 240 changes the state of the indicator 240 (e.g., makes an e-ink image visible again). The indicator 240 will retain its state until another voltage is applied via wire 102, or sufficient charge leaks out of the charge-holding structure 250.

However, if contacts 221, 222 are still connected together through the skin of subject 38, the rectifier 971 will be bypassed by that parallel resistance. As a result, the indicator 240 will either not change state during this process, or will only change state briefly and then will change back. This difference permits operator 42 to command controller 986 to run a test sequence. Operator 42 can then visually inspect each electrode 900 and immediately see whether contact has been lost on that electrode.

In various examples, electrode 900 is connected via two wires 102, 982, one to each contact 221, 222, respectively. Rectifier 971 can be omitted from these examples, or connected in series with a resistor. Controller 986 controls switch 980 to selectively open wire 982 or short wire 982 to ground (shown) or another known potential. Switch 980 can also selectively connect wire 982 to a voltage source (not shown), fixed or variable, under controller of the controller 986. In this way, contact of electrode 900 can be tested by performing the following steps, which the controller 986 is adapted (e.g., programmed) to perform. Supply 905 brings contact 221 to a known voltage. Controller 986 closes switch 980 to bring contact 222 via wire 982 to a known voltage lower than the voltage on contact 221. If there is not a low-resistance DC path between contacts 221, 222, the applied voltages will charge charge-holding structure 250

(FIG. 2) and indicator 240 will change state. If there is such a path, charge-holding structure 250 (FIG. 2) will not charge and indicator 240 will not change state. If there is a path, but it is very high-resistance, indicator 240 will change state, then will change state again when switch 980 is opened as charge leaks out of charge-holding structure 250. In various aspects, series resistor 983 in series with wire 982 (or wire 102) limits the current flowing through any DC path between contacts 221, 222.

According to at least one embodiment, an electrocardiogram system includes a plurality of wires and a plurality of inventive electrodes 900. A measurement unit (e.g., ECG unit 1086, FIG. 10) measures respective voltages on the plurality of wires and produces one or more difference signal(s) indicating the voltage difference between the two of the measured wires. The measurement until includes or is operatively associated with a controller 986 that is adapted to test electrode contact using respective rectifiers 971, as described above.

Figure 11:
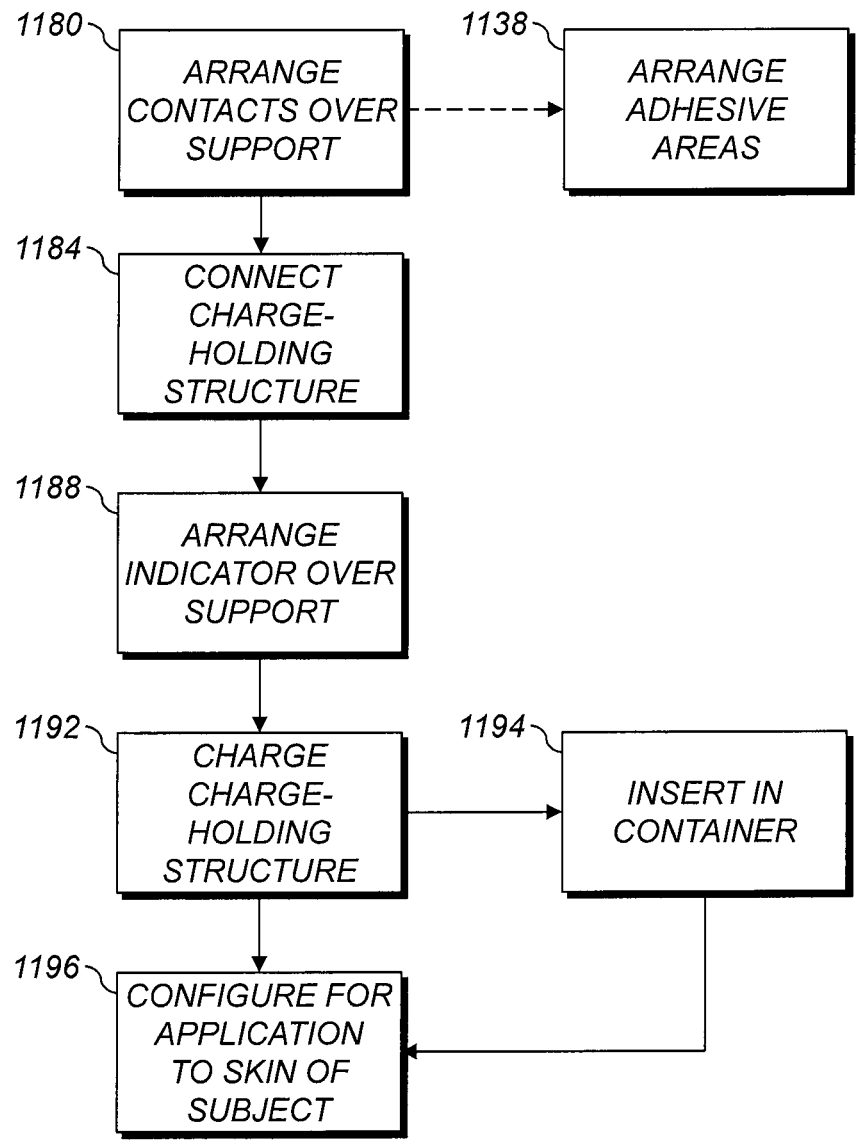
FIG. 11 is a flowchart of methods of making a patient-contact device for a medical sensing system according to various aspects.

FIG. 11 is a flowchart of methods of making a patient-contact device for a medical sensing system according to various aspects. The patient-contact device can be a skin-contact biopotential electrode. Processing begins with step 1180.

In step 1180, separate first and second electrical contacts are arranged over a support. Step 1180 is followed by step 1184. In various aspects, step 1180 includes step 1138. In step 1138, respective areas of conductive adhesive are arranged over the support for the first and second electrical contacts. In the example shown in FIG. 3, step 1180 can include arranging or depositing layers 311, 312, 321, 322 over the support. Step 1138 can include applying or depositing conductive adhesive layers 313, 323 to layers 312, 322.

In step 1184, a charge-holding structure is electrically connected between the first and second electrical contacts. Step 1184 is followed by step 1188.

In step 1188, an indicator is arranged over the support. The indicator is disposed so that it is operatively coupled, by arrangement, structure, or otherwise to the charge-holding structure. In this step, the indicator is formed so that it will change state, e.g., change visibly, in response to a change in the charge stored in the charge-holding structure, as described above. This step can include depositing an electrochromic or other e-ink active layer over the support. This step can also include successively depositing an electrode layer, an e-ink layer, and another electrode layer over the support. Step 1188 is followed by step 1192.

In step 1192, the charge-holding structure is charged so that the indicator has a first visual appearance. This can be performed using a voltage or current source, and the charge-holding structure can be placed into a known state by this step. This step can optionally be performed by inserting the patient-contact device into a container such as that described above with reference to FIG. 8 (step 1194). Container-insertion step 1194 can also be performed after step 1192. Steps 1192 or 1194 can be followed by step 1196.

In step 1196, the patient-contact device with the charge-holding structure in the known state is configured for application to the skin of a subject. As a result, when the electrode is properly applied, the charge-holding structure at least partly discharges through the first electrical contact, the subject's skin, and the second electrical contact, and the indicator changes state. For example, the indicator can take on a second visual appearance different from the first visual appearance. The second indication can be a blank, i.e., the lack of a first indication, as discussed above.

PARTS LIST FOR FIGS. 1-12

38 subject
42 operator
101 electrode
103 wire
186 electrocardiogram (ECG) unit
200 electrode
210 support
221 contact
222 contact
231 terminal
240 indicator
250 charge-holding structure
252 charge-transport unit
255 subject side
295 non-subject side
311 conductive layer
312 stabilizing layer
313 gel layer
321 conductive layer
322 stabilizing layer
323 gel layer
331 via
380 release liner
381, 382 electrical terminal
410 support
411 via
412 conductive adhesive
421, 422 conductor
440 indicator
500 electrode
510 support
512 via
522 electrode
531 terminal
540 indicator
610 aperture
710 voltage source
721, 722 electrode
800 biopotential electrode
821, 822 contact
840 indicator
850 receptacle
855, 856 pair of rails
861, 862 conductor
870 electrical supply
880 release liner
881, 882 conductor
905 time-varying electrical supply
910 electrode
915 reference-voltage supply
919 ground connection
971 rectifier
972 capacitance
980 switch
982 wire
983 resistor
986 controller
1000 electrode
1086 ECG unit
1138 arrange adhesive areas step
1180 arrange-contacts step
1184 connect-structure step 1188 arrange-indicator step
1192 charge-structure step
1194 insert-in-container step
1196 apply-to-subject step
1200 electrode
1260 non-biopotential sensor
1261 output interface The invention is inclusive of combinations of the aspects or embodiments described herein. References to "a particular aspect" and the like refer to features that are present in at least one aspect of the invention. Separate references to "an aspect" or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected by a person of ordinary skill in the art within the spirit and scope of the invention. Examples of variations, combinations, and modifications that are intended to be within the scope of the claims are those having structural elements that do not differ from the literal language of the claims and those including equivalent structural elements with insubstantial differences from the literal language of the claims.

What is claimed is:

1. An electrode, comprising:
   a support having a subject side and a non-subject side opposite the subject side, wherein when the electrode is removably attached to a skin surface of a subject, the subject side is oriented generally facing the subject;
   first and second electrical contacts adapted to contact the skin surface of the subject, wherein at least a portion of the support spaces the first and second electrical contacts apart from the non-subject side;
   a charge-holding structure of the electrode electrically connected, in series, between the first and second electrical contacts and configured to store a charge, wherein:
   the charge-holding structure is at least partly (1) embedded in the support, (2) disposed on the subject side of the support, or (3) disposed on the non-subject side of the support; and
   the charge-holding structure is configured to, in response to an electrical connection between the first electrical contact and the second electrical contact through the subject, dissipate at least some of the charge stored in the charge-holding structure through the subject; and
   an indicator arranged so that at least a portion of the support spaces the indicator away from the subject side of the support, wherein the indicator is:
   electrically connected to the charge-holding structure; and
   configured to visibly change state in response to a change in the charge stored in the charge-holding structure.

2. The electrode according to claim 1, wherein:
   the charge-holding structure comprises spaced-apart first and second conductors disposed at least partly in or on the support and electrically connected to the first and second electrical contacts, respectively; and
   the at least one indicator comprises an electronic ink located at least partly between the first and second conductors and controlled at least partly by a magnitude of charge between the first and second conductors.

3. The electrode according to claim 2, wherein:
   the electronic ink is at least partly (1) embedded in the support, or (2) contained by the support; and
   at least one of the first conductor or the second conductor is spaced apart from the non-subject side by at least part of the support.

4. The electrode according to claim 3, wherein:
   the second conductor is spaced apart from the subject side by at least part of the support; and
   the electrode further comprises a via through the support that electrically connects the second conductor to the second electrical contact.

5. The electrode according to claim 1, wherein the second electrical contact surrounds the first electrical contact.

6. The electrode according to claim 1, wherein the first and second electrical contacts are positioned so that neither surrounds the other.

7. The electrode according to claim 1, wherein the non-subject side of the support comprises an aperture arranged with respect to the indicator so that, when the electrode is removably attached to the skin surface, the indicator is visible through the aperture.

8. The electrode according to claim 1, wherein the indicator is:
   substantially monochromatic;
   adapted to visibly show a first indication when the charge-holding structure is holding a first selected charge; and
   adapted to visibly show a second indication different from the first indication when the charge-holding structure is holding a second, different selected charge.

9. The electrode according to claim 8, wherein the first indication comprises first text and the second indication comprises second, different text.

10. The electrode according to claim 1, further comprising a release liner having respective electrical terminals electrically connected to the first and second electrical contacts, respectively.

11. The electrode according to claim 1, further comprising a charge-transport unit associated with the electrode and electrically connected between the first and second electrical contacts.

12. The electrode according to claim 1, wherein the electrode is an electrocardiogram (ECG) patient-contact electrode.

13. The electrode according to claim 1, wherein the indicator comprises an electrochromic display element.

14. The electrode according to claim 1, wherein each of the first and second electrical contacts comprises conductive adhesive.

15. The electrode according to claim 1, further comprising an electrical terminal electrically connected to the first electrical contact.

16. The electrode according to claim 15, wherein at least a portion of the support spaces the electrical terminal apart from the subject side of the support.

17. The electrode according to claim 1, further comprising a non-biopotential sensor and an output interface adapted to provide information sensed by the non-biopotential sensor.

18. The electrode according to claim 17, wherein the non-biopotential sensor is adapted to sense the temperature of the skin surface of the subject when the electrode is removably attached to the skin surface of the subject.

19. The electrode according to claim 1, further comprising an electrical supply associated with the electrode, the electrical supply configured to maintain a voltage difference between the first and second contacts while the electrode is stored in a container.

20. The electrode according to claim 1, further comprising a rectifier disposed at least partly in or on the support.

21. The electrode according to claim 20, wherein the rectifier is electrically connected so that its forward-conduction direction is from the first electrical contact to the second electrical contact.

22. The electrode according to claim 1, wherein the second electrical contact is positioned so that the second electrical contact has a capacitive electrical connection with the subject upon at least one of:
   improper application of the electrode to the skin surface; and
   partial peeling of the electrode off the skin surface after proper application.

23. The electrode according to claim 20, wherein the rectifier comprises a diode.

24. The electrode according to claim 3, wherein at least one of the first conductor or the second conductor comprises a transparent conductive electrode.

25. An electrode, comprising:
   a support having a subject side and a non-subject side opposite the subject side, wherein when the electrode is removably attached to a skin surface of a subject, the subject side is oriented generally facing the subject;
   first and second electrical contacts adapted to contact the skin surface of the subject, wherein at least a portion of the support spaces the first and second electrical contacts apart from the non-subject side;
   a charge-holding structure of the electrode electrically connected, in series, between the first and second electrical contacts and configured to store a charge, wherein:
   the charge-holding structure is at least partly (1) embedded in the support, (2) disposed on the subject side of the support, or (3) disposed on the non-subject side of the support; and
   the charge-holding structure is configured to, in response to an electrical connection between the first electrical contact and the second electrical contact through the subject, dissipate at least some of the stored charge in the charge-holding structure through the subject; and
   an indicator arranged so that at least a portion of the support spaces the indicator away from the subject side of the support, wherein the indicator is:
   electrically connected to the charge-holding structure;
   controlled by a charge between the first and second electrical contacts;
   configured to visibly change state in response to a change in the charge stored in the charge-holding structure; and
   positioned with respect to the support to be at least partly visible from the non-subject side of the support.

26. The electrode according to claim 25, wherein the support comprises an aperture at least partly in the non-subject side of the support so that the indicator is visible from the non-subject side of the support through the aperture.

27. The electrode according to claim 25, further comprising a transparent conductive electrode located at least partly between the indicator and the support.

28. The electrode according to claim 25, further comprising a non-biopotential sensor and an output interface adapted to provide information sensed by the non-biopotential sensor.

* * * * *